Figure 1:
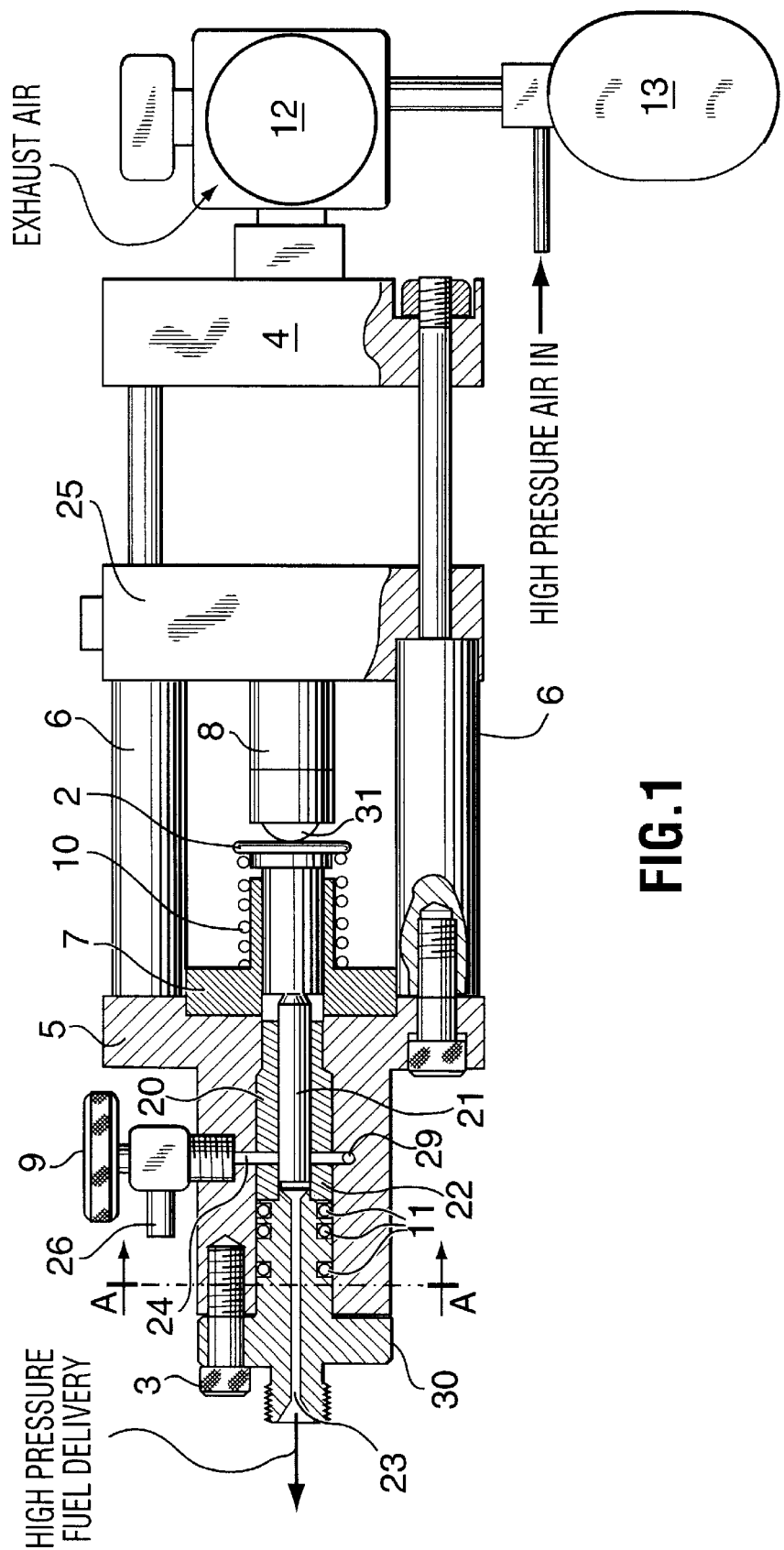

United States Patent [19]
Hole et al.

[11] Patent Number: 5,906,190
[45] Date of Patent: May 25, 1999

[54] AIR-ASSISTED FUEL INJECTION SYSTEM FOR IGNITION QUALITY DETERMINATION

[75] Inventors: Norman J. Hole, Vars; Geoffrey A. Rotheram, Crysler; Gary D. Webster, Ottawa, all of Canada

[73] Assignee: Advance Engine Technology, Ontario, Canada

[21] Appl. No.: 08/980,273

[22] Filed: Nov. 28, 1997

[51] Int. Cl.[6] .................................................. G01N 33/22
[52] U.S. Cl. .......................................... 123/531; 73/35.02
[58] Field of Search ........................... 73/35.02; 123/531; 44/903

[56] References Cited

U.S. PATENT DOCUMENTS

| | | | |
|---|---|---|---|
| 3,575,039 | 4/1971 | Beal ....................................... | 73/35.02 |
| 3,604,405 | 9/1971 | Maher ...................................... | 123/446 |
| 3,661,540 | 5/1972 | Green et al. ............................ | 73/35.02 |
| 3,949,595 | 4/1976 | Jones et al. ............................. | 73/35.02 |
| 4,402,212 | 9/1983 | Childs .................................... | 73/35.02 |
| 4,640,251 | 2/1987 | Harada et al. ......................... | 123/406.3 |
| 4,771,754 | 9/1988 | Reinke ................................... | 123/533 |
| 5,457,985 | 10/1995 | Cellier et al. ........................... | 73/35.02 |

*Primary Examiner*—Erick R. Solis
*Attorney, Agent, or Firm*—Marks & Clerk

[57] ABSTRACT

An ignition quality tester includes an unit for repeatedly injecting a precise quantity of fuel under controlled conditions into a combustion chamber where monitored combustion can be carried out. The tester can be used in an in-line feedback arrangement to permit the continual adjustment of a refining process to maintain the cetane number at a desired value.

9 Claims, 2 Drawing Sheets

AIR-ASSISTED FUEL INJECTION SYSTEM FOR IGNITION QUALITY DETERMINATION

This invention relates to a method and apparatus for testing ignition quality of a fuel, for example, the cetane number of a diesel fuel or middle distillate fuel.

There is a need to measure the cetane numbers, and like parameters, of various kinds of fuel, such as middle distillate fuels. The cetane numbers relate to the ignition delay characteristics, the low temperature starting ability, and the exhaust emission properties of the fuel for a given engine.

Existing techniques involve carrying out combustion tests in a combustion chamber. The fuel must be injected into the chamber under carefully controlled conditions. Prior art methods involve the use of a barrel and plunger, but are not sufficiently well controlled, particular with regard to the quantity of fuel, the rate of injection, and the pressure at which the fuel is injected into the combustion chamber. All these parameters must be very precisely controlled in order to obtain accurate repeatable measurements. Furthermore, prior art techniques do not lend themselves to continual on-line monitoring.

Typical prior art injection systems have poor tolerances and repeatability, particularly of the injection profile, has been very difficult if not impossible to achieve. A multitude of problems arise when trying to inject accurately small quantities of fuel.

An object of the invention is to alleviate the aforementioned problems of the prior art.

According to the present invention there is provided a fuel injection system for ignition quality determination, comprising a nozzle for repeatedly injecting a precise quantity of fuel under controlled conditions into a combustion chamber; a barrel and plunger for feeding said precise quantity of fuel into said nozzle; an in-line piston powered by compressed fluid for actuating said plunger; means for controlling the temperature of the fuel in said nozzle; and pressure-controlled fuel supply means for supplying fuel to said barrel.

The compressed fluid can conveniently be, for example, compressed air at 175 psi. The air may be repeatedly released by a pilot valve to actuate the plunger periodically, for example, five times per minute.

The use of an in-line piston ensures concentric loading on the plunger. This has proved important to achieve repeatability, which is one of the problems associated with the prior art. It is also desirable to have the piston act directly on the plunger to ensure positive contact.

The temperature control of the fuel can be effected with a heater in the barrel. This ensures that the fuel is at a constant viscosity, which also contributes to the repeatability achieved by the invention.

Resonances causing pulsations have proved to be a problem, and these can be avoided by suitable dimensioning of the barrel and plunger.

The combustion process may be monitored by sensors connected to a computer. The tester is particular suitable for in-line continual monitoring of cetane numbers or like parameters, for example in a refinery, so that adjustments can be made to the refining process on a continual feedback basis to maintain the cetane numbers at a desired value The invention will now be described in more detail, by way of example, only with reference to the accompanying drawings, in which:—

Figure 2:
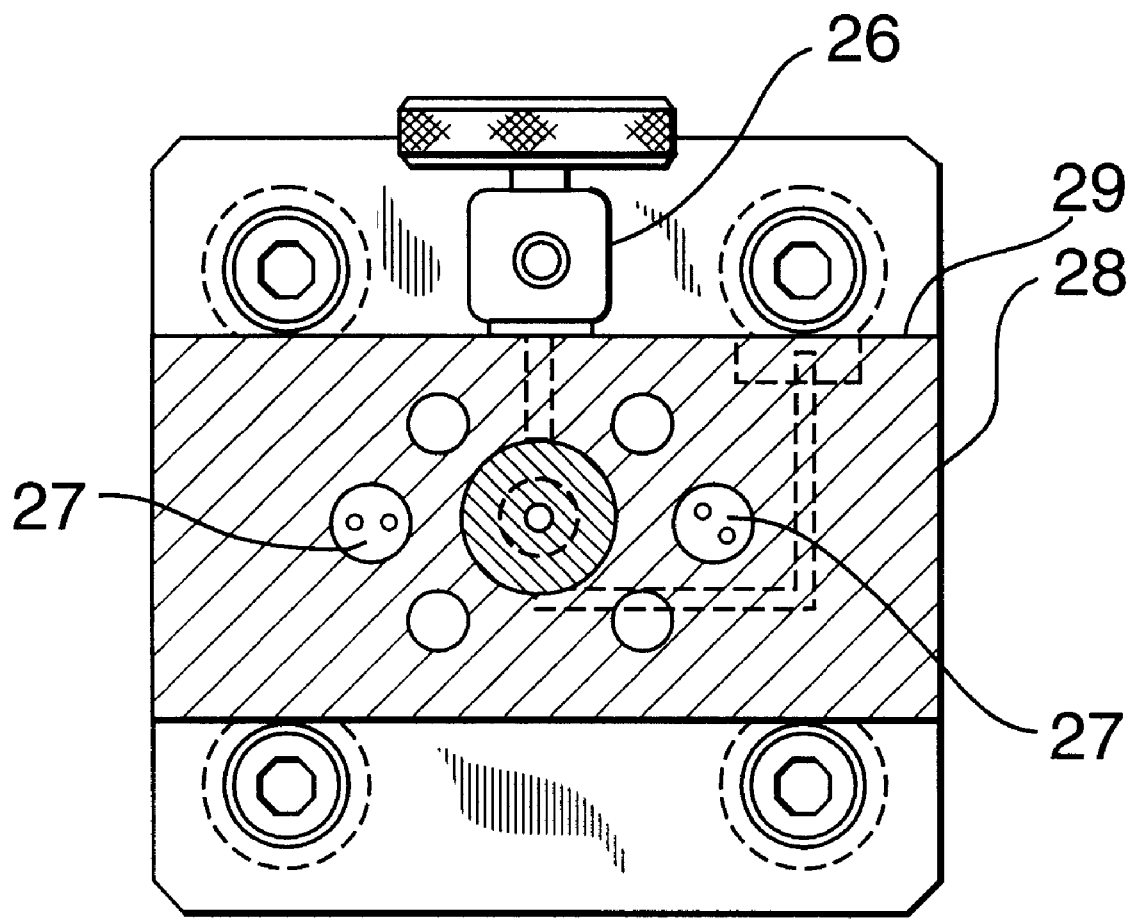

FIG. 1 is a longitudinal cross section of modular fuel injection unit for use in an ignition quality tester in accordance with the invention; and FIG. 2 is a cross section of the injection unit taken along the lines A—A in FIG. 1.

The modular injection unit shown in FIG. 1 injects fuel through a nozzle 30 into a test bombe (not shown) providing a combustion chamber where ignition takes place.

The injection unit comprises a pump block 5 with a cylindrical bore 22 containing a barrel 20 and plunger 21. The plunger 21 faces a narrow channel 23 in nozzle 30 attached to the barrel 20 with clamp 3. The channel 23 communicates with the test bombe and extends into the bore 22. Seals 11 prevent leakage past the body of the barrel clamp 3.

A nylon cam follower 2, in the form of a disk slidable in follower guide 7 extending into the cylindrical bore 22, is biased outwardly by spring 10 and is attached to the near end of the plunger 21.

A bleed valve 9 communicates through channel 24 with the cylindrical bore to bleed off excess fuel.

The pump body 5 is separated from actuator unit 25 by spacers 6 which ensure a rigid coupling. The actuator includes an air cylinder 4 containing a piston (not shown) with a protruding piston rod 8.

Air is stored in container 13 at a pressure of 175 p.s.i. and periodically released, typically at the rate of five times per minute, by a signal from a controller into air cylinder 4 by pilot-operated solenoid valve 12. This causes piston rod 8 to strike the cam follower 2 through ball contact 31 with considerable force, driving home the plunger 21 and causing it to inject fuel into the bombe at a pressure in the region of 175 psi. The ball contact 31 is important in that it helps to ensure concentric loading, which as mentioned above has proved important to obtain good repeatability of the injection profile.

On the return stroke, a limited and precise quantity of fuel is drawn from supply 29, which is maintained a controlled pressure of 50 psi through the channel 28 on the lower side of the bore 22. Any entrapped air is bled from the pump unit by bleed valve 9. The channels are preferably manufactured to fine tolerances using electric discharge machining (EDM).

When the fuel delivery is complete, the solenoid valve 12 is switched to exhaust air in cylinder 4 to atmosphere, and piston rod 8 and plunger 1 return under the action of spring 10 to the stand-by condition.

Two 110 VAC heaters 27 maintain a constant temperature in the pump block 5. A thermocouple continually monitors the temperature of the pump block 5 and the output is used to control the heaters. The pump block 5 is normally heated to 35° C.+/−1° C. This is important to ensure constant viscosity of the fuel.

The above-described unit is capable of delivering 0.10 g of fuel within +/−)0.5% per cycle and can run without maintenance or adjustments for thousands of cycles at five cycles per minute. It can accurately inject fuels with cetane numbers from 15 to 100 and viscosities of all available commercial fuels. The construction can be made simple with a minimum number of moving parts. Each unit can be modular so that it can be bench tested and calibrated for installation on original equipment or supplied as a replacement exchange unit for equipment in the field. Used units may be re-cycled by over-haul and recalibration.

The key components, such as the barrel and plunger, are preferably machine using electric discharge machining (EDM) to achieve fine tolerances.

The unit can be easily purged and bled when changing to fuels of differing specifications.

The described arrangement overcomes the problems of the prior art in that the various elements act together to provide a fuel injection unit that gives good repeatability of injection profile and does not suffer from pulsations and other undesirable effects. It is easy to calibrate. The small dimensions of the passages and the overall construction permit the elimination of dead spaces before the system is re-charged.

We claim:

1. A fuel injection system for ignition quality determination, comprising:

a nozzle for repeatedly injecting a precise quantity of fuel under controlled conditions into a combustion chamber;

a barrel and plunger for feeding said precise quantity of fuel into said nozzle;

an in-line piston powered by compressed fluid for actuating said plunger;

means for controlling the temperature of the fuel in said nozzle;

and pressure-controlled fuel supply means for supplying fuel to said barrel.

2. A fuel injection system as claimed in claim 2, wherein said piston is powered by compressed air.

3. A fuel injection system as claimed in claim 3, further comprising a pilot valve for repeatedly releasing the air to actuate the plunger periodically.

4. A fuel injection system as claimed in claim 1, wherein a cam follower is located on the outboard end of said plunger, and said piston has a ball contact that strikes said cam follower to actuate the plunger.

5. A fuel injection system as claimed in claim 1, wherein a return spring acts on said cam follower to bias said plunger toward the piston after fuel injection.

6. A fuel injection system as claimed in claim 1, wherein said means for controlling the temperature comprises heaters arranged in the barrel.

7. A fuel injection system as claimed in claim 6, further comprising a temperature sensor for controlling said heaters to maintain a constant temperature.

8. A fuel injection system as claimed in claim 1, further comprising a computer connected to sensors for monitoring the combustion process.

9. A fuel injection system as claimed in claim 8, which is connected to an outlet of a refinery and connected for the in-line continual monitoring of cetane numbers or like parameters, so that adjustments can be made to the refining process on a continual feedback basis to maintain said numbers at a desired value.

* * * * *